United States Patent [19]

Miyashita et al.

[11] 4,260,608

[45] Apr. 7, 1981

[54] MAYTANSINOIDS, PHARMACEUTICAL COMPOSITIONS THEREOF AND METHODS OF USE THEREOF

[75] Inventors: Osamu Miyashita, Osaka; Hiroshi Akimoto, Nishinomiya, both of Japan

[73] Assignee: Takeda Chemical Industries, Ltd., Osaka, Japan

[21] Appl. No.: 92,953

[22] Filed: Nov. 9, 1979

[30] Foreign Application Priority Data

Nov. 14, 1978 [JP] Japan ................................ 53/139994

[51] Int. Cl.$^3$ ................. C07D 498/16; A61K 31/535
[52] U.S. Cl. ..................... 424/248.54; 260/239.3 P
[58] Field of Search ................. 260/239.3 P; 424/248.54

[56] References Cited

U.S. PATENT DOCUMENTS

| | | | |
|---|---|---|---|
| 3,896,111 | 7/1975 | Kupchan et al. | 260/239.3 T |
| 4,137,230 | 1/1979 | Hashimoto et al. | 260/239.3 P |

OTHER PUBLICATIONS

Hanka et al., "Microbial Agents and Chemotherapy", vol. 6, No. 5, Nov. 1974, pp. 651–652.
Kupchan et al., "J. Am. Chem. Soc.", vol. 97, No. 18, Sep. 1975, pp. 5294–5295.
Higashide et al., "Nature", vol. 270, pp. 721–722, Dec. 1977.
Wani et al., "J.C.S. Chem. Comm." 1973, p. 390.
Kupchan et al., "J. Med. Chem." (1978), vol. 21, No. 1, pp. 31–37.

*Primary Examiner*—Robert T. Bond
*Attorney, Agent, or Firm*—Wegner & Bretschneider

[57] ABSTRACT

Novel maytansinoids of the formula:

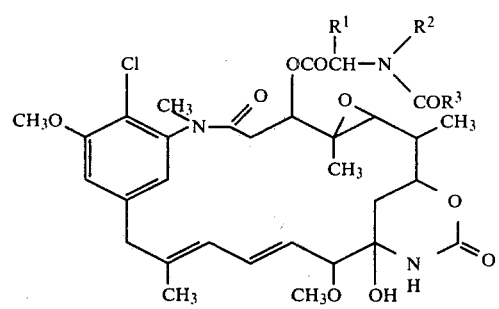

wherein
$R^1$ is hydrogen atom, an alkyl group which may optionally be substituted or a group of the formula: —$A^1$—$Y^1$ wherein $A^1$ is an alkylene group or a bond, and $Y^1$ is a cycloalkyl, phenyl, indolyl or imidazolyl group which may optionally be substituted,
$R^2$ is hydrogen atom, an alkyl, cycloalkyl or benzyl group,
$R^3$ is hydrogen atom, an alkyl group which may optionally be substituted, alkoxy, bornyloxy, isobornyloxy, benzyloxy group or a group of the formula: —$A^2$—$Y^2$ wherein $A^2$ is an alkylene group or a bond, and $Y^2$ is an alicyclic hydrocarbon, phenyl or heterocyclic group which may optionally be substituted,
provided that $R^3$ is not an unsubstituted $C_{1-4}$ alkyl group when both $R^1$ and $R^2$ are methyl groups, have antimicrobial antimitotic and antitumor activities.

10 Claims, No Drawings

MAYTANSINOIDS, PHARMACEUTICAL COMPOSITIONS THEREOF AND METHODS OF USE THEREOF

This invention provides maytansinoid compounds of the following formula (I):

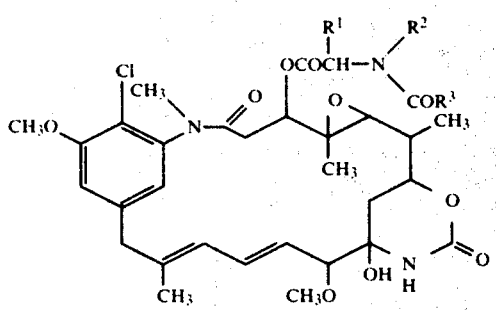

wherein $R^1$ is hydrogen atom, an alkyl group which may optionally be substituted, or a group of the formula —$A^1$—$Y^1$ ($A^1$ is an alkylene or a bond, $Y^1$ is a cycloalkyl, phenyl, indolyl or imidazolyl group which may optionally be substituted); $R^2$ is hydrogen atom, an alkyl, cycloalkyl, cycloalkylalkyl or benzyl group; $R^3$ is hydrogen atom, an alkyl group, which may optionally be substituted, alkoxy, bornyloxy, isobornyloxy, benzyloxy group or a group of the formula —$A^2$—$Y^2$ ($A^2$ is an alkylene group or a bond; $Y^2$ is an alicyclic hydrocarbon, phenyl or heterocyclic group which may optionally be substituted); provided that $R^3$ is not an unsubstituted $C_{1-4}$ alkyl groups when both $R^1$ and $R^2$ are methyl groups.

Referring to the above formula (I), the alkyl groups $R^1$, $R^2$ and $R^3$ may, for example, be alkyl groups of about 1 to 7 carbon atoms (e.g. methyl, ethyl, propyl, isopropyl, butyl, isobutyl, sec-butyl, tert-butyl, pentyl, isopentyl, 1-methylpropyl, 2-ethylbutyl, hexyl, heptyl, etc.).

The alkylene groups designated by $A^1$ and $A^2$ may, for example, straight-chain or branched alkylene groups of 1 to 4 carbon atoms (e.g. methylene, ethylene, methylmethylene (ethylidene), propylene, ethylmethylene, butylene, 1- or 2-methylethylene, 1-, 2- or 3-methylpropylene, 1- or 2-ethylethylene, propylmethylene, 1,1- or 1,2-dimethylethylene, isopropylmethylene, etc.).

The cycloalkyl groups for $Y^1$ and $R^2$ may, for example, by cycloalkyl groups of about 3 to 7 carbon atoms (e.g. cyclopropyl, cyclobutyl, cyclopentyl, cyclohexyl, cycloheptyl, etc.).

The cycloalkylalkyl group for $R^3$ includes, for example, $C_{3-7}$ cycloalkyl-$C_{1-4}$ alkyl groups (e.g. cyclopropylmethyl, cyclobutylmethyl, cyclopentylmethyl, cyclohexylmethyl, cyclopropylethyl, cyclopropylpropyl, cyclobutylethyl, cyclobutylpropyl, cyclopentylethyl, etc.).

The alkoxy group for $R^3$ may, for example, be an alkoxy group of about 1 to 7 carbon atoms, preferably about 1 to 4 carbon atoms (e.g. methoxy, ethoxy, propoxy, isopropoxy, butoxy, isobutoxy, sec-butoxy, tert-butoxy, etc.).

The alicyclic hydrocarbon group for $Y^2$ may, for example, be a cycloalkyl or cycloalkenyl group of about 3 to 7 carbon atoms. As examples of the cycloalkyl may be mentioned the cycloalkyls named for $R^2$. Examples of said cycloalkenyl of 3 to 7 carbon atoms include 1-cyclobutenyl, 1-,2- or 3-cyclopentyl, 1-, 2- or 3-cyclohexenyl, 4-cycloheptenyl, 4-cyclooctenyl, 1,4-cyclohexadienyl, 4-norbornenyl, 2,4,6-cycloheptatrienyl, etc.

As examples of heterocylic group $Y^2$, there may be mentioned N, O or/and S-containing 4-, 5- or 6-membered heterocyclic groups which may be saturated or unsaturated, a benzene ring being optionally fused thereto. Examples of such N-containing 4-, 5- or 6-membered heterocyclic groups include azetidinyl, pyridyl, 1,2,3,4-tetrahydropyridyl, piperidyl, quinolyl, 1,2-dihydroquinolyl, 3- or 4-isoquinoyl, 1,2-dihydroisoquinolyl, pyrrolyl, pyrrolinyl, pyrrolidinyl, indolyl, etc. Examples of said O-containing 5- or 6-membered heterocyclic groups include furyl, pyranyl, dihydropyranyl, benzofuryl, benzopyranyl, etc. Among said S-containing 5- or 6-membered heterocyclic groups are thienyl, benzothienyl and so forth. Said heterocyclic group may have from 2 to 4 hetero-atoms, which may be the same or different and any of N, O or/and S. Thus, there may be mentioned, among others, imidazolyl, pyrazolyl, pyrazinyl, pyrimidyl, pyridazinyl, 2-imidazolyl, imidazolidinyl, benzimidazolyl, indazolyl, quinoxalyl, quinazolynyl, cinnolynyl, 1,4-dioxanyl, 1,4-benzodioxanyl, 1,2- or 1,3-dithiolanyl, 1,3-dithianyl, isoxazolyl, oxazolyl, morpholinyl, benzisoxazolyl, benzoxazolyl, isothiazolyl, thiazolyl, benzoisothiazolyl, benzothiazolyl, benzothiadinyl, 1,2,4-, 1,2,5- or 1,3,4-oxadiazolyl, 1,2,3-, 1,2,4-, 1,2,5- or 1,3,4-thiadiazolyl, 1,2,3-, 1,2,5- or 1,3,4-triazolyl, 1,3,5-triazinyl, benzotriazolyl, 1,2,3,4-tetrazolyl, etc.

Among these heterocyclic groups, those containing NH group, such as azetidinyl, 1,2,3,4-tetrahydropyridyl, piperidyl, 1,2-dihydroquinolyl, 1,2-dihydroisoquinoyl, pyrrolyl, pyrrolinyl, pyrrolidinyl, pyrazolyl, 2-imidazolinyl, imidazolidinyl, indazolyl, morpholinyl, 1,2,3-, 1,2,5- or 1,3,4-triazolyl, benzotriazolyl, 1,2,3,4-tetrazolyl, etc., generally preferably have a suitable substituent, such as those mentioned hereinafter, in the N-position or have the alkylene chain $A^2$ attached to the N-position.

The alkyl groups $R^1$ and $R^3$ may be substituted by such groups as, for example, alkoxy groups of 1 to 4 carbon atoms (e.g. methoxy, ethoxy, propoxy, isopropoxy, butoxy, isobutoxy, sec-butoxy, tert-butoxy, etc.), alkanoyl groups of 2 to 4 carbon atoms (e.g. acetyl, propionyl, butyryl, isobutyryl, etc.), alkanoyloxy groups of 2 to 4 carbon atoms (e.g. acetyloxy, propionyloxy, butyryloxy, isobutylyloxy, etc.), alkoxycarbonyl groups of 2 to 4 carbon atoms (e.g. methoxycarbonyl, ethoxycarbonyl, propoxycarbonyl, isopropoxycarbonyl, etc.), halogen atoms (e.g. chlorine, fluorine, bromine, iodine), nitro, cyano, trifluoromethyl, di-$C_{1-4}$-alkylamino groups (e.g. dimethylamino, diethylamino, dipropylamino, diisopropylamino, dibutylamino, etc.), alkylthio groups (e.g. methylthio, ethylthio, propylthio, isopropylthio, butylthio, isobutylthio, sec-butylthio, tert-butylthio, etc.), methylsulfinyl, methylsulfonyl, oxo, thioxo, $C_{1-4}$-alkanoylamido groups (e.g. formamido, acetamido, propionylamido, butyrylamino, isobutyrylamido, etc.) and so forth.

One to 3 of these substituent groups may be present, and may be the same or different.

When $R^1$ and $R^2$ in formula (I) are both methyl, the alkyl group $R^3$ is preferably a substituted alkyl.

The cycloalkyl, phenyl, indolyl and imidazolyl as represented by $Y^1$ and the alicyclic hydrocarbon group (e.g. cycloalkyl, cycloalkenyl), phenyl and heterocyclic group as represented by $Y^2$ may also have substitutents which may, for example, be the groups mentioned as optional substituents on alkyl groups as $R^1$ and $R^3$, as well as alkyl groups of 1 to 4 carbon atoms (e.g. methyl, ethyl, propyl, isopropyl, butyl, isobutyl, sec-butyl, tert-butyl). One to 3 of such substituents may be present, and may be the same or different.

As examples of the substituted $C_{1-7}$ alkyls as represented by $R^1$ and $R^3$, there may be mentioned methoxymethyl, butoxymethyl, methylthiomethyl, methylthioethyl, ethylthioethyl, isopropylthioethyl, butylthioethyl, isobutylthioethyl, acetyloxymethyl, acetyloxyethyl, ethoxycarbonylmethyl, butoxycarbonylethyl, fluoromethyl, chloromethyl, chloroethyl, 3-chloropropyl, 4-chlorobutyl, 3,3,3-trichloropropyl, trifluoromethyl, bromomethyl, 4-bromobutyl, 5-bromopentyl, iodomethyl, 2-iodoethyl, 1,1-dimethyl-2,2-dichloroethyl, 2-chloro-1-chloromethyl-1-methylethyl, cyanomethyl, methylsulfinylethyl, methylsulfonylmethyl, etc.

The substituted $C_{3-7}$ cycloalkyl groups as represented by $Y^1$ and $Y^2$ include, among others, 2,2-dimethylcyclopropyl, 2-propylcyclopropyl, 2-butylcyclopropyl, 4-isobutylcyclohexyl, 2-bromocyclopropyl, 2-chlorocyclobutyl, 4-chlorocyclohexyl, 2-iodocyclohexyl, 2,2-difluorocyclobutyl, 3-methoxycyclohexyl, 2,2-dimethyl-3-acetylcyclobutyl, 4-acetylcyclohexyl, 2-cyanocyclohexyl, 2-cyanocyclobutyl, 4-cyanocyclohexyl, 4-dimethylaminocyclohexyl, etc.

The substituted $C_{3-7}$ cycloalkenyl group as represented by $Y^2$ include, among others, 2-cyano-2-cyclohexenyl, 3,3-dimethyl-4-cyclobutenyl, 4-ethoxycarbonyl-1-cyclohexenyl, 4-butoxycarbonyl-1-cyclohexenyl, etc.

The substituted phenyl groups as represented by $Y^1$ and $Y^2$ include, among others, 2-, 3- or 4-methylphenyl, 4-tert-butylphenyl, 2-, 3- or 4-chlorophenyl, 2-, 3- or 4-bromophenyl, 2-, 3-or 4-iodophenyl, 2-, 3- or 4-fluorophenyl, 2- or 4-methoxyphenyl, 4-butoxyphenyl, 4-methoxycarbonylphenyl, 3-acetylphenyl, 2-, 3- or 4-nitrophenyl, 3- or 4-cyanophenyl, 4-dimethylaminophenyl, 4-diethylaminophenyl, 4-acetoxyphenyl, 4-butyryloxyphenyl, 2,4-, 2,5-, 2,6-, 3,4- or 3,5-dichlorophenyl, 3,4-dimethoxyphenyl, 3,4,5-trimethoxyphenyl, 3,4-methylenedioxyphenyl, 3-trifluoromethylphenyl, 4-methylthiophenyl-4-methylsulfonylphenyl, 4-acetamidophenyl, etc.

The substituted indolyl as represented by $Y^1$ includes 5-bromo-2-indolyl, 5-chloro-2-indolyl, 5-fluoro-2-indolyl, 5-methoxy-2-indolyl, 1-methyl-2-indolyl, 5-methyl-2-indolyl, etc. The substituted imidazolyl group as represented by $Y^1$ includes 1-methyl-5-imidazolyl, 3-methyl-5-imidazolyl, 2-methyl-4-imidazolyl, etc. As examples of the substituted or unsubstituted 4-, 5- or 6-membered heterocyclic group as represented by $Y^2$, there may be mentioned 1-acetyl-2-azetidinyl, 1-methyl-2-pyrrolyl, 3-methoxy-2-furyl, 3-methyl-2-furyl, 5-methyl-2-furyl, 5-nitro-2-furyl, 3-methyl-2-thienyl, 3-bromo-4, 5-dimethyl-2-thienyl, 2-methyl-4-thiazolyl, 1,2-dimethyl-4-chloro-5-imidazolyl, 1-butyl-4-pyrazolyl, 2,4-dichloro-4-isothiazolyl, 5-methyl-1,2,3-thiadiazol-4-yl, 3,5-dimethyl-4-isoxazolyl, 2-methyl-5-diisopropylamino-4-oxazolyl, 5-methyl-1,2,5-oxadiazol-3-yl, 4-methoxy-1,2,5-oxadiazol-3-yl, 5-methyl-1,3,4-oxadiazol-2-yl, 3-methyl-1,2,3-thiadiazol-5-yl, 3-methyl-1,2,3-thiadiazol-5-yl, 5-methyl-1,3,4-thiadiazol-2-yl, 5-methyl-1,2,3-thiadiazol-4-yl, 1-methyl-1,2,3-triazol-4-yl, 2-ethyl-1,2,3,4-tetrazol-5-yl, 5-nitro-2-pyridyl, 6-ethyl-4-pyridyl, 5-ethoxycarbonyl-3-pyridyl, 5-chloro-3-pyridyl, 1-butyryl-2-piperidyl, 2-oxo-5-pyranyl, 7-methoxy-3,4-dihydro-2H-2-pyranyl, 1-acetyl-2-pyrrolidinyl, 1-propyl-5-oxo-3-pyrrolidinyl, 3-methyl-2,4-dioxo-5-thiazolidinyl, 4-, 5-, 6- or 7-nitro-3-indolyl, 5-fluoro-2-indolyl, 2-methyl-5-methoxy-3-indolyl, 1-methyl-2-indolyl, 5-chloro-2-benzothienyl, 3-methyl-2-benzofuryl, 1-methyl-2-benzimidazolyl, 6-nitro-2-benzothiazolyl, 4-chloro-3-quinolyl, 6-methoxy-2-quinolyl, 2,4-dimethoxy-3-quinolyl, 2-methyl-1-oxo-3-isocarbostyryl, 7-methyl-coumaryl, 4-methylquinazolyl, 3-propyl-2,4-dioxo-5-imidazolinyl, 7-methoxycarbonyl-2-oxo-1,2-dihydro-3-quinazolyl, 2-furyl, 2-thienyl, 3-isoxazolyl, 4-imidazolyl, 1,2,5-thiadiazolyl-3-yl, 2-, 3- or 4-pyridyl, 2-pyradinyl, 2-pyrimidinyl, 2-s-triazinyl, 1,2-dithioranyl, 3-indolyl, 2-benzothienyl, 2-benzofuryl, 3-benzopyrazolyl, 2-benzimidazolyl, 2-benzoxazolyl, 3-benzisoxazolyl, 3-benzisothiazolyl, 2-benzothiazolyl, 2-benzo-1, 4-oxadinyl, 3-quinolyl, 1-isoquinolyl, etc.

As shown in the formula (I), when $A^1$ or $A^2$ is an alkylene chain, $Y^1$ or $Y^2$ is attached to the α-carbon atom or N-carbonyl group, respectively, of the N-substituted aminoacetyloxy side chain in 3-position of maytansinol through said alkylene chain, and when $A^1$ or $A^2$ represents a bond, $Y^1$ or $Y^2$ is directly attached to said α-carbon atom or N-carbonyl group, respectively.

As examples of the group corresponding to the alkylene chain $A^1$ or $A^2$ to said cycloalkyl, phenyl or heterocyclic group $Y^1$ or $Y^2$ (that is, $—A^1—Y^1$ or $—A^2—Y^2$), there may be mentioned adamantylmethyl, cyclohexylmethyl, 3-cyclohexylpropyl, 2-cyclopentenylmethyl, 2-cyclopentylethyl, etc. The $—A^1—Y^1$ or $—A^2—Y^2$ when it is an aralkyl group, includes 4-bromobenzyl, 2-, 3- or 4-chlorobenzyl, 2,5- or 3,4-dimethoxybenzyl, 4-ethoxybenzyl, 4-fluorobenzyl, 3- or 4-methoxybenzyl, 4-methoxyphenylethyl, 1- or 2-naphthylmethyl, 2-, 3- or 4-nitrobenzyl, 3-nitrophenethyl, benzyl, 2-, 3- or 4-phenylpropyl, 2-,3- or 4-methylbenzyl, 3,4,5-trimethoxybenzyl, α-methylphenethyl, etc.

When $—A^1—Y^1$ or $—A^2—Y^2$ represents a heterocyclealkyl group, it may, for example, be 5-ethyl-3-indolylmethyl, 5-fluoro-3-indolylmethyl, 3-indolylmethyl, 3-indolyl-3-propyl, 5-methoxy-3-indolylmethyl, 5-methyl-3-indolylmethyl, 2-,3- or 4-pyridylmethyl, 4-(2-thienyl)propyl, 1- or 5-tetrazolylmethyl, 2-benzothiadiazolylmethyl, 2-benzoxazolylmethyl, 3-benzisothiazolylmethyl, 2-(1-piperidinyl)ethyl or the like.

The heterocycle-alkyl group corresponding to said alkylene chain $A^2$ attached to the N-atom of said N-containing heterocyclic group $Y^2$ (that is, $—A^2—Y^2$) may, for example, be 1-pyrrolylmethyl, 2-oxo-1-pyrrolidinylmethyl, 1-imidazolylmethyl, 3,5-dimethyl-1-pyrazolylmethyl, 1-piperidylethyl, 4-morpholinylmethyl, 1-tetrazolylmethyl, 2,5-dioxo-1-pyrrolidinylmethyl, 1,3-dioxo-2-isoindolylmethyl, 2-thioxo-4-oxo-3-thiazolidinylmethyl, 3,5-diiodo-4-oxo-1, 4-dihydropyridine-1-methyl, 4-methyl-1-piperazinylmethyl, 1-indolylethyl or the like.

Where $R^1$ and $R^2$ in formula (I) are both methyl, $R^3$ is preferably aralkoxy or phenyl group.

Referring, further, to the formula (I), the N-acyl-α-aminoacyl group, in which $R^1$, $R^2$ and $R^3$ have been defined hereinbefore, is typically exemplified by N-acetyl-N-methylglycyl, N-benzoyl-N-methylglycyl, N-(4-chlorobenzoyl)-N-methylglycyl, N-acetyl-N-benzylalanyl, N-acetyl-N-methylleucyl. N-acetyl-N-methylphenylalanyl, 2-(N-acetyl-N-methyl)-3-methoxycarbonylpropyl, 2-(N-acetyl-N-methyl)-3-methylmercaptopropionyl, 2-(N-acetyl-N-methyl)-3-ethylmercaptopropionyl, $N^\alpha$-acetyl-$N^\alpha$, $N'$-dimethylhistidinyl, N-acetyl-N-methylisoleucyl, N-acetyl-N-methylleucyl, N-acetyl-N-methylmethionyl, N-acetyl-N-methylphenylalanyl, N-acetyl-N-methyltryptophanyl, N-acetyl-N-methyl-4'-acetoxytyrosinyl, N-benzyl-N-methylvalyl, N-acetyl-N-methylphenylglycyl, N-isonicotinoyl-N-methyl-$\alpha$-aminobutyryl, N-acetyl-N-methyl-3-cyanoalanyl, N-acetyl-N-methyl-$\alpha$-(2-thiazolyl)glycyl, N-acetyl-N-methyl-(4'-dimethylaminophenyl)alanyl, etc.

In the above-mentioned compound (I), desirable is a compound of the formula (I) wherein $R^1$ is hydrogen atom, a $C_{1-7}$ alkyl group which may optionally be substituted, or a group of the formula: $-A^1-Y^1$ wherein $A^1$ is a $C_{1-4}$ alkylene group or a bond, and $Y^1$ is a $C_{3-7}$ cycloalkyl, phenyl, indolyl or imidazolyl group which may optionally be substituted, $R^2$ is hydrogen atom, a $C_{1-7}$ alkyl, $C_{3-7}$ cycloalkyl, $C_{3-7}$ cycloalkyl-$C_{1-4}$ alkyl or benzyl group, and $R^3$ is hydrogen atom, a $C_{1-7}$ alkyl group which may optionally be substituted, $C_{1-4}$ alkoxy, bornyloxy, isobornyloxy, benzyloxy group or a group of the formula:

$$-A^2-Y^2$$

wherein $A^2$ is a $C_{1-4}$ alkylene group or a bond, and $Y^2$ is a $C_{3-7}$ alicyclic hydrocarbon, phenyl or 4-, 5-, 6-membered heterocyclic group which may have a fused benzene ring, which may optionally be substituted, provided that $R^3$ is not an unsubstituted $C_{1-4}$ alkyl group when both $R^1$ and $R^2$ are methyl groups.

The maytansinoid compound of formula (I) can be produced by acylating maytansinol with an $\alpha$-amino acid derivative of formula (II) in the presence of a carbodiimide.

(II)

wherein $R^1$, $R^2$ and $R^3$ are as previously defined

The amino acid derivative (II), of which D- and L-isomers exist, either of the D- and L-compounds or an optionally proportioned mixture thereof may be utilized with success.

When an optically active amino acid derivative residue is introduced into the 3-hydroxy group of maytansinol according to this reaction, the corresponding optically active amino acid (II) may be preferably employed. There are, however, cases in which even with such an optically active amino acid derivative (II), the maytansinoid compound (I) is produced as a mixture of the D- and L-forms.

The amino acid derivative (II) can normally be used in a proportion of about 1 to 500 molar equivalents, and preferably about 1 to about 30 equivalents, based on maytansinol. The carbodiimide can be used in a proportion of about 1 to 700 molar equivalents, preferably about 1 to 50 equivalents based on maytansinol.

In many cases, the reaction according to this invention is desirably conducted in the presence of a catalyst which is able to promote acylation of maytansinol with amino acid derivative (II). The catalyst may be an appropriate acid or base. The acid catalyst includes, among others, Lewis acids [e.g. anhydrous zinc chloride, anhydrous aluminum chloride ($AlCl_3$), anhydrous ferric chloride, titanium tetrachloride ($TiCl_4$), stannic tetrachloride ($SnCl_4$), antimony pentachloride, cobalt chloride, cupric chloride, boron trifluoride etherate, etc.], inorganic strong acids (e.g. sulfuric acid, perchloric acid, hydrochloric acid, hydrobromic acid, etc.), organic strong acids (e.g. benzenesulfonic acid, p-toluenesulfonic acid, trifluoroacetic acid, trichloroacetic acid, etc.), acidic ion exchange resins (e.g. polystyrenesulfonic acid), etc. The basic catalyst includes, among others, tertiary amine compounds (e.g. pyridine, α-, β- or γ-picoline, 2,6-lutidine, 4-dimethylaminopyridine, 4-(1-pyrrolidinyl)pyridine, dimethylaniline, diethylaniline, triethylamine, N-methylmorpholine, etc.), halogenated alkali metals (e.g. potassium fluoride, anhydrous lithium iodide, etc.), salts of organic acids (e.g. sodium acetate, etc.) and so forth. Among these catalysts, anhydrous zinc chloride is particularly advantageous in many instances. The catalyst is used in a catalytically sufficient amount to promote acylation of maytansinol with amino acid derivative (II), e.g. about 0.001 to about 10 molar equivalents, and preferably about 0.01 to about 1 equivalent, based on amino acid derivative (II). The use of such a catalyst leads in many cases to a remarkably improved yield of maytansinoid compound (I). The amount of amino acid derivative required may also be reduced. Thus, in many cases, the relative amount of (II) with respect to maytansinol may be reduced to about 1 to 6 molar equivalents.

The carbodiimide compound which can be used for the production of compounds of this invention need only contains a carbodiimide bonds (—N=C=N—) which is transformable into a urea bond (—NH—CO—NH—) in the course of the present acylation reaction. Thus, compounds represented by the following formula, for instance, may be utilized.

$$R^4-N=C=N-R^5 \quad (III)$$

wherein $R^4$ and $R^5$ each represents an organic acid residue such that its carbodiimide bond is transformable into a urea bond during the acylation reaction. The organic residues $R^4$ and $R^5$ may be,, for example, selected from among $C_{3-7}$ cycloalkyl groups optionally having di-lower ($C_{1-6}$; the same definition applies hereinafter) alkylamino; a lower alkyl group optionally having di-lower alkylamino or morpholino; and a phenyl group optionally having lower alkyl.

The carbodiimide is preferably dicylohexylcarbodiimide for practical purposes, although such other carbodiimides may also be employed as, for example, diphenylcarbodiimide, di-o-tolylcarbodiimide, di-p-tolylcarbodiimide, di-tert-butylcarbodiimide, 1-cyclohexyl-3-(2-morpholinoethyl)carbodiimide, 1-cyclohexyl-3-(4-diethylaminocyclohexyl)carbodiimide, 1-ethyl-3-(2-diethylaminopropyl)carbodiimide and 1-ethyl-3-(3-dimethylaminopropyl)carbodiimide.

This acylation reaction may be carried out in a suitable solvent. Among such solvents are esters (e.g. ethyl acetate), ethers (e.g. diethyl ether, dioxane, tetrahydrofuran), halogenated hydrocarbons (e.g. methylene chloride, chloroform), nitriles (e.g. acetonitrile), aromatic hydrocarbons (e.g. benzene), nitromethane, pyridine, dimethylformamide, dimethylsulfoxide, sulfolane, etc. and suitable mixtures of such solvents.

This reaction may be conducted normally at temperatures from ice-cooling to the reflux temperature of the system.

The maytansinoid compound (I) thus produced can be easily isolated by subjecting the reaction mixture to a conventional purification procedure such as concentration, solvent extraction, chromatography, recrystallization, etc. When maytansinoid compound (I) is produced as a mixture of D- and L-compounds, the isomers can be separated from each other generally by a conventional procedure, e.g. silica gel column chromatography. The maytansinoid compound (I) according to this invention includes such individual isomers and any mixture of the isomers.

The maytansinoid compounds (I) according to this invention have potent antimitotic and antitumor activities with comparatively low toxicity and are therefore suited for administration, oral or parenterally, the tumour-bearing warm-blooded animals (e.g. mouse, rat, rabbit, dog, cat and man) for the purpose of prolonging their survival times. Each compound (I) is normally administered in the form of a pharmaceutical preparation (e.g. injectable solution) as formulated with a carrier, diluent or the like which is known per se.

When compound (I) is administered in the form of an injectable preparation, it may be given subcutaneously, intraperitoneally, intravenously or intramuscularly, for instance. The dosage of compound (I) varies with the kind, symptom, administration route, etc. but, for example, in case of intravenous administration for prolonging life span of the animal suffering from leukemia or melanoma, it may be decided from the range of about 1 to 1000 $\mu$g/kg body weight, preferably about 5 to 200 $\mu$g/kg body weight per dose.

The injectable preparation can be prepared by the established pharmaceutical procedure; for example by dissolving about 50 $\mu$g to 3 mg of compound (I) in each about 0.5 ml of alcohol (e.g. ethanol), followed by addition of a sufficient amount of physiological saline to make a total of 10 ml. When a small dosage is indicated, the above solution may be further diluted with physiological saline.

The maytansinoid compounds (I) according to this invention are of value also in that they have antimicrobial activity, e.g. antifungal and antiprotozoal properties. Thus, for example, the maytansinoid compounds (I) are useful for teating *Tetrahymena pyriformis* W. As an antifungal or antiprotozoal agent, compound (I) is instrumental in assays of the bacterial flora of soil, active sludge, animal body fluids, etc. Thus, for the isolation of useful bacteria from soil samples or in the assay of activity of bacteria to the exclusion of those of protozoa and fungi in connection with the operation and analysis of active sludge systems for waste water treatment, the compound (I) can be advantageously employed to ensure selective growth of bacteria without permitting growth of the concomitant protozoa and fungi.

Thus, such a sample is added to a liquid or solid medium, and per milliliter of the inoculated medium, 0.1 ml of a 1% methanol-water solution of about 10 to 100 $\mu$g/ml of compound (I) is added, and then incubated to let the bacteria grow and multiply.

The maytansinoid compound (I), in an amount of 0.02 ml of a 1 mg/ml aqueous solution, is able to inhibit growth of causative microorganisms of stem rot, helminthosporium leaf rot and sheath blight in rice plants, for instance, and can therefore be used for the treatment of such plant diseases. The procedure may comprise dissolving compound (I) in 1% aqueous methanol to a concentration of about 0.5 to 5 $\mu$g/ml and spraying rice plants with the solution.

The starting compound maytansinol as used in the production of compounds (I) according to this invention is a known compound as a plant constituent (Kupchan et al., J. Amer. Chem. Soc. 97, 5294(1975)) and can be also obtained by reductive cleavage of maytansine or its analogs.

Maytansinol may also be advantageously produced by cultivating an Antibiotic C-15003-producer of the genus Nocardia (FERM-P No.3992, IFO-13726, ATCC-31281) in a culture medium to produce ansamytocin of the following formula (IV) in the culture broth and subjecting the same metabolite to reductive cleavage with a metal hydride such as LiAlH$_4$.[E. Higashide et al., Nature, Vol. 270, 721(1977) or German Offenlegungusschrift No. 2746209 U.S. Pat. No. 4,162,940; Serial No. 811, 448)]

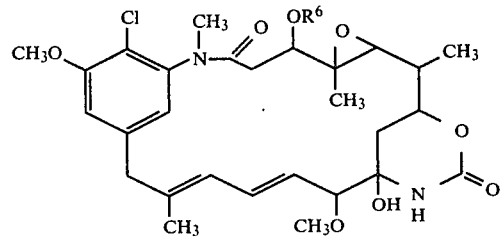

wherein $R^6$ is acetyl, propionyl, isobutyryl, n-butyryl or isovaleryl.

$\alpha$-Amino acid derivative (II) can be produced by a conventional method, as it is or as modified. The following is a partial list of the available literature on such known production methods.

J. R. Coggins, N. L. Benoiton, Can. J. Chem. 49, 1968 (1971)

P. Quitt, J. Hellerback, K. Vogler, Helv. Chim. Acta, 46, 327 (1963)

S. L. Portnova, et al, Zh, Obsch. Khim. 38, 428(1968)

The following examples are intended to illustrate this invention in further detail and should no means be construed as limiting the scope of the invention.

EXAMPLE 1

In 30 ml of dry dichloromethane is dissolved 150.0 mg (0.265 mmol) of maytansinol, and then, 124.0 mg (0.663 mmol) of N-acetyl-N-methyl-L-leucine and 174.2 mg (0.846 mmol) of dicyclohexylcarbodiimide (DCC) are added. The mixture is stirred at room temperature for a while and 46 mg (0.338 mmol) of anhydrous zinc chloride is added. After about 30 minute of stirring at room temperature, an additional 46 mg of anhydrous zinc chloride is added. The mixture is stirred at that temperature for about 45 minutes.

Once again, 104.3 mg (0.558 mmol) of N-acetyl-N-methyl-L-leucine, 141.3 mg of DCC (0.686 mmol) and 46 mg of anhydrous zinc chloride are added, followed by-stirring at the same temperature for 2.5 hours. The reaction mixture is washed with water, the organic layer dried over Na$_2$SO$_4$, the solvent distilled off under reduced pressure. The residue is chromatographed on a silica gel column (75 g) and elution is carried out with ethyl acetate (ca 600 ml) and, then, with H$_2$O-saturated ethyl acetate, the eluate being collected in 17-g fractions. Fractions 14 through 34 are pooled and the solvent is distilled off. The residue (100 mg) is chromatographed for a second time using a silica gel column (35 g) [solvent system: chloroform/methanol=60/1 (v/v)], the eluate being collected in 25-g fractions. Fractions 16 through 30 are pooled, the solvent distilled off, the residue is dissolved in ethyl acetate and after cooling, the resulting crystals are collected by filtration to obtain 89 mg of Compound A. The first chromatographic fractions 35 through 56 are also pooled, the solvent distilled off and the residue chromatographed on silica gel (40 g) [solvent system=Chloroform/methanol=60/1 (v/v), ca 200 ml and=40/1, one liter], the eluate being collected in 25-g fractions.

Fractions 17 through 35 are pooled, the solvent is distilled off and the residue is dissolved in ethyl acetate, followed by addition of ether. The resulting precipitate is recovered by filtration to obtain 52 mg of Compound B. Both Compound A and Compound B are the contemplated compounds of this invention and, based on their physical and chemical properties given below, appear to be maytansinol 3-(N-acetyl-N-methyl)-L-leucine ester and maytansinol 3-(N-acetyl-N-methyl)-D-leucine ester, respectively.

Compound A
m.p. 172°–175° C. (decompn.)

NMR spectrum (CDCl$_3$) δ ppm: 0.80(3H, s), 0.93(3H, d, J=5 Hz), 1.00(3H, d, J=5 Hz), 1.28(3H, d, J=6 Hz), 1.67(3H, s), 2.13(3H, s), 2.14(1H, dd, J=3 Hz & 14 Hz), 2.67(1H, dd, J=11 Hz & 14 Hz), 2.83(3H, s), 3.03(1H, d, J=9 Hz), 3.07(1H, d, J=13 Hz), 3.19(3H, s), 3.35(3H, s), 3.49(1H, d, J=9 Hz), 3.57(1H, s), 3.73(1H, d, J=13 Hz), 3.97(3H, s), 4.25(1H, m), 4.76(1H, dd, J=3 Hz & 11 Hz), 5.38(1H, m), 5.69(1H, dd, J=9 Hz & 14 Hz), 6.24(1H, s), 6.40(1H, dd, J=11 Hz & 14 Hz), 6.71(1H, d, J=11 Hz), 6.82(1H, d, J=1.5 Hz), 6.85(1H, d, J=1.5 Hz), etc.

Mass spectrum (m/e): 733, 716, 690, 672, 657, 640, 637, 630

UV spectrum (λ$_{max}$$^{MeOH}$) nm: 233, 244, 253.5, 281.5, 290

Compound B
m.p.: 157°–159° C. (decompn.)

NMR spectrum (CDCl$_3$) δ ppm: 0.89(3H, s), 1.00(3H, d, J=5.5 Hz), 1.10(3H, d, J=5.5 Hz), 1.28(3H, s), 1.72(3H, s), 2.17(3H, s), 2.18(1H, dd, J=3 Hz & 14 Hz), 2.72(1H, dd, J=11 Hz & 14 Hz), 2.88(1H, d, J=ca 9 Hz), 3.02(3H, s), 3.18(1H, d, J=13 Hz), 3.36(3H, s), 3.46(1H, d, J=9 Hz), 3.47(1H, d, J=13 Hz), 3.99(3H, s), 4.28(1H, m), 4.84(1H, dd, J=3 Hz & 11 Hz), 5.14(1H, s), 5.24(1H, m), 6.03(1H, dd, J=9 Hz & 14 Hz), 6.20(1H, s), 6.27(1H, d, J=10 Hz), 6.46(1H, dd, J=10 Hz & 14 Hz), 6.84(1H, d, J=ca 1.5 Hz), 5.92(1H, d, J=ca 1.5), etc.

Mass spectrum (m/e): 733, 716, 690, 672, 657, 640, 637, 630

UV spectrum (λ$_{max}$$^{MeOH}$)nm: 233, 240(sh), 253, 281, 289

EXAMPLE 2

As in Example 1, to the solution of 150 mg of maytansinol in 30 ml of dry dichloromethane at room temperature, are added 153.4 mg of N-acetyl-N-benzyl-D-alanine, 170.4 mg of DCC and about 70 mg of anhydrous zinc chloride. After 30 minutes, 117.5 mg of N-acetyl-N-benzyl-D-alanine, 128.4 mg of DCC and 42 mg of anhydrous zinc chloride are further added. The mixture is stirred at room temperature for 50 minutes, after which the solvent is distilled off. The residue is dissolved in ethyl acetate, the insolubles are filtered off and the filtrate is washed with water and dried (Na$_2$SO$_4$). The solvent is distilled off, the residue is chromatographed on silica gel (75 g), and elution is carried out with ethyl acetate (1 l) and, then, with H$_2$O-saturated ethyl acetate (750 ml), the eluate being collected in 17-g fractions. Fractions 18 through 45 are pooled, the solvent distilled off and the residue dissolved in a small amount of ethyl acetate and allowed to stand, whereupon crystals separate out. To the system is added ether and, after standing, the crystals are collected by filtration. This procedure yields 39.6 mg of Compound C. Fractions 68 through 85 are pooled and the solvent is distilled off to obtain 95.6 mg of product. This is chromatographed on silica gel (40 g) [solvent system: chloroform/methanol=40/1 (v/v), 1 liter]. Fractions 11 through 20 are pooled, the solvent is distilled off and the residue is dissolved in ethyl acetate, followed by addition of ether. The resulting crystals are collected by filtration to obtain 37.7 mg of Compound D. Based on the date shown below, both Compound C and Compound D appear to be isomers of the contemplated compound maytansinol 3-(N-acetyl-N-benzyl)alanine ester, the sole dissimilarity thereof being in the steric configuration of the substituent in 2'-position.

Compound C
m.p. 174°–177° C. (decompn.)

NMR spectrum (CDCl$_3$) δ ppm: 0.86(3H, s), 1.29(3H, d, J=6 Hz), 1.36(3H, d, J=7 Hz), 1.69(3H, s), 2.17(3H, s), 2.20 (1H, dd, J=3 Hz & 15 Hz), 2.71(1H, dd, J=12 Hz & 15 Hz), 2.93 (1H, d, J=9 Hz), 3.17(3H, s), 3.35(3H, s), 3.43(1H, d, J=9 Hz), 3.57(1H, d, J=13 Hz), 3.98(3H, s), 4.35(1H, m), 4.56(2H, s), 4.62(1H, q, J=7 Hz), 4.98(1H, dd, J=3 Hz & 12 Hz), 5.65(1H, m), ca 6.30(1H, s), 6.31–6.47(2H, m), 6.76(1H, d, J=1-2 Hz), 6.84(1H, d, J=1-2 Hz), 7.31–7.39(5H, m), etc.

Mass spectrum (m/e): 706, 691, 671, 503, 485, 470, 450

UV spectrum (λ$_{max}$$^{MeOH}$)nm: 233, 243(sH), 254, 282, 290

Compound D
m.p. 163°–166° C. (decompn.)

NMR spectrum (CDCl$_3$) δ ppm: 0.90(3H, s), 1.31(3H, d, J=6 Hz), 1.40(3H, d, J=7 Hz), 1.71(3H, s), 2.13(3H, s), 2.23 (1H, dd, J=3 Hz & 15 Hz), 2.70(1H, dd, J=12 Hz & 15 Hz), 2.84 (1H, d, J=9 Hz), 3.09(3H, s), 3.31(1H, d, J=13 Hz), 3.36(3H, s), 3.44(1H, d, J=9 Hz), 3.97(3H, s), 4.35(1H, m), 4.70(2H, q(AB-type)), 4.94(1H, dd, J=3 Hz & 12 Hz), 5.00(1H, q, J=7 Hz), 5.85(1H, dd, J=9 Hz & 14 Hz), 6.17(1H, d, J=11 Hz), ca 6.28(1H, s), 6.45(1H, dd, J=11 Hz & 14 Hz), 6.75(1H, d, J=1-2 Hz), 6.84(1H, d, J=1-2 Hz), 7.18–7.42(5H, m), etc.

Mass spectrum (m/e): 706, 691, 671, 503, 485, 470, 450

UV spectrum (λ$_{max}$$^{MeOH}$)nm: 233.5, 241(sh), 253.5, 281.5, 290

EXAMPLE 3

As in Example 1, 157.4 mg (0.279 m mol) of maytansinol is dissolved in 30 ml of dichloromethane, and at room temperature, 154.5 mg (0.699 mmol) of N-acetyl-N-methyl-L-phenylalanine (AMPA) and 45.5 mg (0.335 mmol) of anhydrous zinc chloride are added. Then, at intervals of about 80 minutes, 133 mg (0.602 mmol) AMPA, 143 mg (0.694 mmol) of DCC and about 50 mg (0.368 mmol) of ZnCl$_2$, and 150.0 mg (0.679 mmol) of AMPA, 122.4 mg (0.599 mmol) of DCC and about 50 mg (0.368 mmol) of ZnCl$_2$ are further added. After these additions, the reaction mixture is stirred for 30 minutes and the solvent is distilled off under reduced pressure. To the residue is added ethyl acetate, the insolubles are filtered off, and the filtrate is washed with water and concentrated under reduced pressure. The residue is chromatographed on silica gel (75 g) [solvent system: ethyl acetate/H$_2$O-saturated ethyl acetate = ½(v/v)], the eluate being collected in 17-g fractions. Fractions 16 through 22 are pooled, the solvent is removed and the residue is chromatographed on silica gel (35 g)[solvent system: chloroform/methanol = 50/1 (v/v), ca 450 ml]. Fractions 13 through 17 are pooled and the solvent is distilled off, whereupon 59.7 mg of residue is obtained. The residue is dissolved in a small amount of ethyl acetate at a slightly elevated temperature, the solution is allowed to stand and, after ether is added, the crystals are recovered by filtration. By the above procedure is obtained 38.7 mg of Compound E. The first chromatographic fractions 30 through 49 are pooled, the solvent is distilled off and the residue is chromatographed on a silica gel column (35 g) [solvent system = chloroform/methanol = 50/1 (v/v)]. Fractions 16 through 30 are pooled, the solvent is distilled off, and after ether is added, the resulting crystals are collected by filtration. By this procedure is obtained 66.0 mg of Compound F. Based on the data presented below, both Compound E and Compound F are the contemplated compound maytansinol 3-(N-acetyl-N-methyl)-phenylalanine ester but are isomers differing from each other only in steric configuration of the 2'-substituent.

Compound E
m.p. 189°–193° C. (decompn.)
NMR spectrum (CDCl$_3$) δ ppm: 0.83(3H, s), 1.27(3H, d, J=7 Hz), 1.65(3H, s), 1.87(3H, s), 2.17(1H, dd, J=3 Hz & 15 Hz), 2.67(1H, dd, J=11 Hz & 15 Hz), 2.71(3H, s), 2.98(1H, d, J=9 Hz), 3.16(3H, s), 3.35(3H, s), 3.47(1H, d, J=9 Hz), 3.58(1H, d, J=13 Hz), 3.95(3H, s), 4.31(1H, m), 4.88(1H, dd, J=3 Hz & 11 Hz), 5.29(1H, m), 5.71(1H, m), 6.2–6.7(3H, m), 6.77(2H, approx. d, J=ca 2 Hz), 7.03–7.43 (5H, m), etc.

Compound F
m.p. 212°–214° C. (decompn.)
NMR spectrum (CDCl$_3$) δ ppm: 0.89(3H, s), 1.27(3H, d, J=6 Hz), 1.67(3H, s), 2.00(3H, s), 2.24(1H, dd, J=3 Hz & 14 Hz), 2.72(1H, dd, J=12 Hz & 14 Hz), 2.90(3H, s), 3.13(3H, s), 3.35(3H, s), 3.45(1H, d, J=9 Hz), 3.48(1H, d, J=13 Hz), 3.96(3H, s), 4.29(1H, m), 4.89(1H, dd, J=3 Hz & 12 Hz), 5.60(1H, dd, J=4.5 Hz & 12 Hz), 5.95(1H, dd, J=9 Hz & 15 Hz), ca 6.17(1H, d, J=ca 11 Hz), 6.23(1H, s), 6.47(1H, dd, J=11 Hz & 15 Hz), 6.77(2H, approx. d, J=ca 2 Hz), 7.08–7.37(5H, m), etc.

EXAMPLE 4

In 30 ml of dry dichloromethane are dissolved 310 mg of maytansinol, 582 mg of N-tert-butoxycarbonyl N-methyl-L-alanine and 549 mg of DCC and the solution is stirred at room temperature for 15 minutes. Then, 207 mg of p-dimethylaminopyridine (DMAP) is added, following by stirring at room temperature overnight. The precipitate is filtered off, the filtrate is diluted with ethyl acetate to make 150 ml and the dilution is washed with a mixture of 50 ml water and 2 ml 1 N-HCl, water (50 ml) and aqueous sodium hydrogen carbonate solution (50 ml) in the order mentioned. The organic layer is taken, dried (Na$_2$SO$_4$) and distilled to remove the solvent. The residue is dissolved in chloroform and chromatographed on a silica gel column (100 g), elution being carried out with chloroform and, then, with chloroform/methanol = 50/1 (v/v) and the eluate being collected in 25-g fractions. Fractions 95 through 97 are pooled and the solvent is distilled off, whereupon 25 mg or product (Fraction 4) is obtained. Fractions 98 through 130 are similarly treated to obtain 82 mg of product (Fraction 5). Since Fractions 4 and 5 are mixtures of two contemplated compounds, they are separated by preparative TLC (PSC-Fertigplatten, Kieselgel 60F$_{254}$, Art. 5715, Merck, West Germany) (developing solvent: H$_2$O-saturated ethyl acetate). By this procedure are obtained 11 mg of Compound H and 8 mg of a substantially equal mixture of Compound H and Compound G from Fraction 4, and 61 mg of Compound G and 7 mg of a substantially equal mixture of Compound G and Compound H from Fraction 5.

Based on the following data, Compound G and Compound H are considered to be maytansinol 3-(N-tert-butoxycarbonyl-N-methyl)-L-alanine ester and maytansinol 3-(N-tert-butoxycarbonyl-N-methyl)-D-alanine ester, respectively.

Compound G
NMR spectrum: 0.79(3H, s), 1.28(3H, d, J=3 Hz), 1.38 (3H, d, J=7 Hz), 1.66(3H, s), 2.13(1H, dd, J=3 Hz & 15 Hz), 2.62(1H, dd, J=12 Hz & 15 Hz), 2.68(3H, s), 3.01(1H, d, J=9 Hz), 3.06(1H, d, J=12 Hz), 3.20(3H, s), 3.34(3H, s), 3.60(1H, broad), 3.70(1H, d, J=12 Hz), 3.99(3H, s), 4.27(1H, m), 4.67(1H, dd, J=3 Hz & 12 Hz), 5.02(1H, q, J=7 Hz), 5.62(1H, dd, J=9 Hz & 14 Hz), 6.34(1H, s), 6.42(1H, dd, J=11 Hz & 14 Hz), 6.72(1H, d, J=11 Hz), 6.80(2H, s), etc.

Mass spectrum (m/e): 750, 688, 632, 588, 573, 486, 485, 450, etc.

UV spectrum: ($\lambda_{max}^{MeOH}$)nm: 234, 244, 254, 282, 290

Compound H
NMR spectrum: 0.83(3H, s), 1.24(3H, d, J=4 Hz), 1.47 (3H, d, J=7 Hz), 1.68(3H, s), 2.18(1H, dd, J=4 Hz & 15 Hz), 2.62(1H, dd, J=12 Hz & 15 Hz), 2.68(1H, d, J=10 Hz), 2.83(3H, s), 3.13(3H, s), 3.13(1H, d, J=13 Hz), 3.31(3H, s), 3.41(1H, d, J=9 Hz), 3.51(1H, d, J=13 Hz), 3.96(3H, s), 4.30(1H, m), 4.78(1H, q, J=7 Hz), 4.85(1H, broad), 4.97(1H, dd, J=4 Hz & 12 Hz), 5.81(1H, dd, J=9 Hz & 13 Hz), 6.21(1H, d, J=11 Hz), 6.26(1H, s), 6.39(1H, dd, J=11 Hz & 13 Hz), 6.75(1H, d, J=2 Hz), 6.82(1H, d, J=2 Hz), etc.

Mass spectrum (m/e): 750, 688, 632, 588, 573, 486, 485,450, etc.

UV spectrum ($\lambda_{max}^{MeOH}$)nm: 234, 241(sh), 253.5, 282, 290

EXAMPLE 5

As in Example 4, 85 mg of maytansinol, 164 mg of N-tert-butoxycarbonyl-N-methyl-D-alanine, 168 mg of DCC and 53 mg of DMAP are mixed in 9 ml of dry dichloromethane. The mixture is stirred at room temperature overnight, the reaction product is extracted with ethyl acetate and the extract is chromatographed on silica gel, whereby 62 mg of a mixture of Compound H and Compound G is obtained. These compounds H and G are found to be identical with the corresponding compounds obtained in Example 4 TLC findings (solvent: H$_2$O-saturated ethyl acetate) suggest that the ratio of two compounds in the mixture is about 4:1.

EXAMPLE 6

As in Example 1, 145.8 mg of maytansinol is dissolved in 23 ml of dry dichloromethane and at 4-hour intervals, 87 mg of N-acetylsarcosine, 164 mg of DCC and about 50 mg of anhydrous zinc chloride are respectively added. The mixture is then stirred at room temperature overnight and, as in Example 1, is extracted with ethyl acetate. The extract is chromatographed on a silica gel column (20 g) (solvent system=ethyl acetate/H$_2$O-saturated ethyl acetate=1/1, v/v), the eluate being collected in 15-g fractions. Fractions 23 through 49 are pooled and the solvent is distilled off, whereupon 45 mg of maytansinol 3-(N-acetyl)sarcosine ester is obtained as a glass-like substance.

NMR spectrum (CDCl$_3$) δ ppm: 0.87(3H, s), 1.28(3H, d, J=5 Hz), 1.68(3H, s), 2.14(3H, s), 2.19(1H, dd, J=3 Hz & 14 Hz), 2.55(1H, dd, J=11 Hz & 14 Hz), 2.76(1H, d, J=9 Hz), 3.07(2H, s), 3.13(3H, s), 3.18(3H, s), 3.35(3H, s), 3.47 (1H, d, J=9 Hz), 3.52(1H, d, J=13 Hz), 3.98(3H, s), 4.18(1H, m), 4.92(1H, dd, J=3 Hz & 11 Hz), 5.74(1H, dd, J=9 Hz & 15 Hz), 6.18(1H, d, J=11 Hz), 6.44(1H, dd, J=11 Hz & 15 Hz), 6.53(1H, s), 6.82(2H, s), etc.

EXAMPLE 7

To 20 ml of dry dichloromethane are added 99.5 mg of maytansinol, 250.6 mg of DCC, 162.4 mg of N-acetylglycine and 88.8 mg of DMAP. The mixture is stirred at room temperature. After 2 hours and 18 hours, respectively, 80.4 mg and 72.1 mg of DMAP are further added and, after another 8 hours, 143.6 mg of DCC and 81.9 mg of N-acetylglycine are further added. The mixture is stirred at room temperature for an additional 2 days. The insolubles are filtered off, the filtrate is concentrated to dryness under reduced pressure and the residue is dissolved in ethyl acetate. After the insoluble matter is filtered off, the filtrate is washed with 0.5 N HCl and, then, with a saturated aqueous solution of sodium hydrogen carbonate and dried (Na$_2$SO$_4$). The solvent is then distilled off and the residue is chromatographed on a silica gel column (40 g) (solvent system: ethyl acetate/H$_2$O-saturated ethyl acetate=2/1, v/v), the eluate being collected in 17-g fractions. Fractions 37 through 67 are pooled and the solvent is distilled off, whereby 76.6 mg of product is obtained. On recrystallization from ethyl acetate-ether, there is obtained 62.1 mg of maytansinol 3-(N-acetyl)glycine ester.

m.p. 189°–192° C. (decompn.)

NMR spectrum (CDCl$_3$) δ ppm: 0.86(3H, s), 1.24(3H), 1.67(3H, s), 2.04(3H, s), 2.18(1H, dd, J=3 Hz & 14 Hz), 2.53 (1H, dd, J=11 Hz & 14 Hz), 2.83(1H, d, J=9 Hz), 3.15(3H, s), 3.36(3H, s), 3.97(3H, s), 4.15(2H, ABq), 4.27(1H, m), 4.90(1H, dd, J=3 Hz & 11 Hz), 5.68(1H, dd, J=8 Hz & 14 Hz), 6.21(1H, d, J=11 Hz), 6.45(1H, dd, J=11 Hz & 14 Hz), 6.77(1H, d, J=ca 1.5 Hz), 5.85(1H, d, J=ca 1.5 Hz), etc.

Mass spectrum (m/e): 663, 602, 587, 567, 560, 503, 485, 470, 450, etc.

EXAMPLE 8

Maytansinol (300 mg), N-t-butyloxycarbonyl-phenylglycine (1.55 g), DCC(1.27 g) and DMAP (135 mg) are mixed in dry dichloromethane (20 ml) and the mixture is stirred at room temperature. The reaction mixture is worked up as in Example 7 and the crude product obtained is chromatographed on a silica gel column (solvent system: chloroform/methanol=100/1, v/v) to give 0.277 g of maytansinol 3-(N-t-butyloxycarbonyl)-L-phenyl glycine ester (compound I) and 0.06 g of maytansinol 3-(N-t-butyloxycarbonyl)-D-phenylglycine ester (compound J)

Compound I

Mass spectrum (m/e): 736, 735, etc.

NMR spectrum: 0.74(3H, s), 1.24(3H, d), 1.38(9H, s), 1.54(3H, s), 2.72(3H, s), 3.33(3H, s), 3.81(3H, s), 7.30(2H, m), 7.36(3H, m), etc.

Compound J

Mass spectrum (m/e): 736, 735, etc.

NMR spectrum: 0.71(3H, s), 1.18(3H, d), 1.33(9H, s), 1.62(3H, s), 3.19(3H, s), 3.33(3H, s), 3.87(3H, s), 7.33 (5H, s), etc.

EXAMPLE 9

To a solution of 185.2 mg of maytansinol in 30 ml of dry dichloromethane, N-benzoyl-N-methyl-DL-alanine (407 mg), DCC (473 mg) and ZnCl$_2$ (ca.110 mg) are added and the reaction mixture is stirred at room temperature for 4 hours. The reaction mixture is worked up as in Example 1. The crude product obtained is chromatographed on a silica gel column (75 g) with ethyl acetate to give 88 mg (fraction 1) and 136 mg (fraction 2) of products. Fraction 1 is recrystallized from ethyl acetate-ether to give 53.4 mg of maytansinol 3-(N-benzoyl-N-methyl)-L-alanine ester (compound K). Fraction 2 is rechromatographed on a silica gel column (75 g) (solvent system: chloroform/methanol=40/1, v/v) to give 71 mg of product, which is recrystallized from ethyl acetate-n-hexane to give 53.3 mg of maytansinol-3-(N-benzyl-N-methyl)-D-alanine ester (compound L).

Compound K m.p. 188°–195° C. (decompn.)

Mass spectrum (m/e): 694, etc.

Compound L m.p. 170°–173° C. (decompn.)

Mass spectrum (m/e): 694, etc.

EXAMPLE 10

Maytansinol (282 mg), N-t-butyloxycarbonyl-L-phenylalanine (795 mg), DCC (618 mg) and DMAP(127 mg) are mixed in 20 ml of dry dichloromethane and the mixture is stirred at room temperature for 30 minutes. The reaction mixture is worked up as in Example 7 and the crude product is chromatographed on a silica gel column(20 g) with, at first, chloroform and then chloroform/methanol=100/1 (v/v) as solvent, to give 170 mg of maytansinol 3-(N-t-butyloxycarbonyl)-L-phenylalanine ester (compound M) and 110 mg of maytansinol 3-(N-t-butyloxycarbonyl)-D-phenylalanine ester (compound N).

Compound M

NMR spectrum: 0.82(3H, s), 1.26(3H, d), 1.39(9H, s), 1.67(3H, s), 3.15(3H, s), 3.29(1H, s), 3.96(1H, s), 6.81(1H, d), 6.93(1H, d), 7.12–7.23(5H, m), etc.

Compound N

NMR spectrum: 0.80(3H, s), 1.21(3H, d), 1.13(9H, s), 1.62(3H, s), 3.21(3H, s), 3.37(1H, s), 3.92(1H, s), 6.73(1H, d), 6.82(1H, d), 7.22(5H, s), etc.

EXAMPLE 11

Maytansinol (225.6 mg), N-t-butyloxycarbonylglycine (420 mg), DCC (495 mg) and DMAP(106.7 mg) are made to react in 20 ml of dry dichloromethane at room temperature for 5 minutes. The reaction mixture is worked up as in Example 7 and the crude product is chromatographed on silica gel column (20 g) (solvent system: chloroform/methanol=98/2, v/v) to give 204 mg of maytansinol 3-N-t-butyloxycarbonylglycine ester.

Mass spectrum (m/e): 721, 660, 604, etc.

NMR spectrum: 0.80(3H, s), 1.28(3H, d), 1.63(3H, s), 1.43(9H, s), 3.13(3H, s), 3.33(3H, s), 3.95(3H, s), 4.07(3H, s), etc.

EXPERIMENTAL DATA

Antitumor activity

Therapeutic tests were carried out in mice according to NCI-protocol 1,300, Cancer Chemother, Reports, Part 3, 1972, Vol. 3, No. 2, in which melanoma B-16 tumor cells had been intraperitoneally transplanted, compound (I) being administered intraperitoneally once daily for 9 consecutive days. Life span prolongations obtained are shown in Table 1 as T/C % values.

TABLE 1

| Compound | Dose (μg/kg) | Antitumor activities B-16 (T/C %) |
|---|---|---|
| Maytansinol 3-(N-acetyl-N-methyl)-L-leucine ester | 200 | 65 |
| | 100 | 202 |
| | 50 | 209 |
| | 25 | 171 |
| Maytansinol 3-(N-acetyl-N-methyl)-L-phenylalanine ester | 200 | 95 |
| | 100 | 205 |
| | 50 | 208 |
| | 25 | 211 |
| Maytansinol 3-(N-t-butoxy-carbonyl-N-methyl)-L-alanine ester | 100 | 193 |
| | 50 | 198 |
| | 25 | 178 |
| | 12.5 | 163 |

ANTIPROTOZOAL ACTIVITY

Antiprotozoal activity of compound (I) was assayed with *Tetrahymena pyriformis* W as the test organism and a medium composed of 20 g tryptose-peptone (Difco Co.), 1 g yeast extract, 2 g glucose, 1000 ml distilled water, 10 ml 1 M phosphate buffer (pH 7.0) as the assay medium. The microorganism was incubated at 28° C. for 44 to 48 hours and the growth inhibitory activity of compound (I) was assayed by the serial dilution method. The minimal inhibitory concentrations of compound (I) are shown in Table 2.

TABLE 2

| Compound | Configuration of amino acid part | Antiprotozoal activity MIC μg/ml *Tetrahymena pyriformis* W |
|---|---|---|
| Maytansinol 3-(N-acetyl-N-methyl)leucine ester | (L) | 2 |
| | (D) | 28 |
| Maytansinol 3-(N-acetyl-N-methyl)phenylalanine ester | (L) | 1 |
| Maytansinol 3-(N-t-butoxy-carbonyl-N-methyl)alanine ester | (L) | 0.4-0.8 |
| | (D) | 8 |
| Maytansinol 3-(N-benzoyl-N-methyl)alanine ester | (L) | 2-4 |
| Maytansinol 3-(N-t-butoxy-carbonyl)phenyl alanine ester | (L) | 4 |

Examples of Pharmaceutical Compositions

Example A

| Composition for Injection | |
|---|---|
| (1) Maytansinol 3-(N-t-butoxycarbonyl-N-methyl)-L-alanine ester | 50 mg |
| (2) Ethanol | 10 g |
| (3) Polysorbate 80 (Tween 80) | 40 g |
| (4) Mannitol | 20 g |
| (5) Distilled water, a sufficient quantity to make | 1000 ml |

Preparation (1) is dissolved in (2). To this solution, (3) and (4) are added, followed by the addition of sterilized distilled water to make 1000 ml of the solution. Ten milliliter each of the solution is used to fill 100 amber ampoules and the air within the ampoules is replaced with nitrogen gas, then the ampoule is sealed. All the processes are conducted under sterile conditions.

Example B

| Composition for Injection | |
|---|---|
| (1) Maytansinol 3-(N-acetyl-N-methyl)-L-phenylalanine ester | 100 mg |
| (2) Ethanol | 5 g |
| (3) Polysorbate 80 (Tween 80) | 100 g |
| (4) Mannitol | 20 g |
| (5) Distilled water, a sufficient quantity to make | 1000 ml |

Preparation

By a similar procedure to that of Example A, an injectable solution of (1) is prepared.

What is claimed is:

1. A compound of the formula:

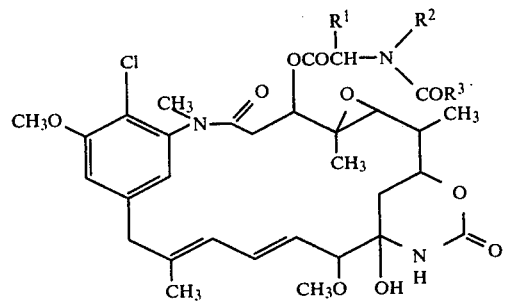

wherein
R$^1$ hydrogen, C$_{1-7}$ alkyl, or —A$^1$—Y$^1$;
A$^1$ is C$_{1-4}$ alkylene or a single covalent bond;
Y$^1$ is a C$_{3-7}$ cycloalkyl, phenyl, indolyl or imidazolyl group,
R$^2$ is hydrogen, C$_{1-7}$ alkyl, C$_{3-7}$ cycloalkyl, C$_{3-7}$ cycloalkyl-C$_{1-4}$ alkyl or benzyl;
R$^3$ is C$_{1-4}$ alkoxy, bornyloxy, isobornyloxy, benzyloxy or —A$^2$—Y$^2$;
A$^2$ is C$_{1-4}$ alkylene or a single covalent bond; and
Y$^2$ is C$_{3-7}$ alicyclic hydrocarbon or phenyl.

2. A compound of the formula:

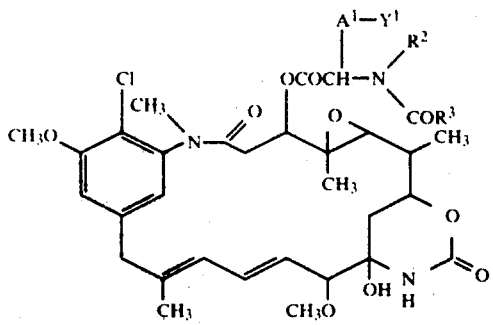

wherein

A¹ is $C_{1-4}$ alkylene or a single covalent bond;

Y¹ is $C_{3-7}$ cycloalkyl, phenyl, indolyl or imidazolyl;

R² is hydrogen, $C_{1-7}$ alkyl, $C_{3-7}$ cycloalkyl, $C_{3-7}$ cycloalkyl-$C_{1-4}$ alkyl or benzyl;

R³ is hydrogen, $C_{1-7}$ alkyl, $C_{1-4}$ alkoxy, bornyloxy, isobornyloxy, benzyloxy group or -A²-Y²;

A² is a $C_{1-4}$ alkylene group or a single covalent bond; and

Y² is a $C_{3-7}$ alicyclic hydrocarbon or phenyl.

3. A compound of the formula:

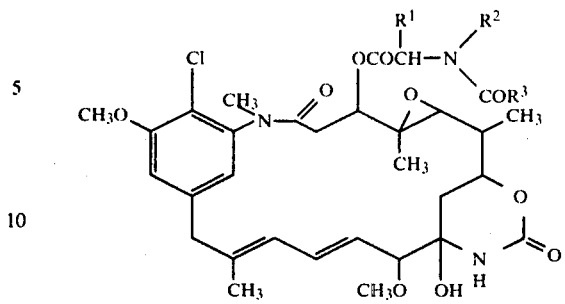

wherein

R¹ is $C_{4-7}$ alkyl;

R² is hydrogen, $C_{1-7}$ alkyl, $C_{3-7}$ cycloalkyl, $C_{3-7}$ cycloalkyl-$C_{1-4}$ alkyl or benzyl;

R³ is hydrogen, $C_{1-7}$ alkyl, $C_{1-4}$ alkoxy, bornyloxy, isobornyloxy, benzyloxy group or -A²-Y²;

A² is $C_{1-4}$ alkylene or a single covalent bond; and

Y² is $C_{3-7}$ alicyclic hydrocarbon or phenyl.

4. A compound according to claim 2 or 3, wherein R³ is a $C_{1-4}$ alkyl, $C_{1-4}$ alkoxy or phenyl group.

5. Maytansinol 3-(N-acetyl-N-methyl)leucine ester.

6. Maytansinol 3-(N-acetyl-N-methyl)phenylalanine ester.

7. Maytansinol 3-(N-tert-butoxycarbonyl-N-methyl)alanine ester.

8. A pharmaceutical composition for inhibiting the growth of tumor cells and prolonging the survival time or a tumor-bearing warm-blooded animal which comprises as an active ingredient an effective amount of a compound of claim 4, 5, 6, 7, 1, 2 or 3.

9. A method for inhibiting the growth of tumor cells in a warm-blooded animal which comprises administering to said warm-blooded animal an effective amount of a compound of claim 4, 5, 6, 7, 1, 2, or 3.

10. A method for prolonging the survival time of a tumor-bearing warm-blooded animal which comprises administering to said warm-blooded animal an effective amount of a compound of claim 4, 5, 6, 7, 1, 2 or 3.

* * * * *